US012661637B2

(12) United States Patent
Dhachapally et al.

(10) Patent No.: US 12,661,637 B2
(45) Date of Patent: Jun. 23, 2026

(54) ALKANE DEHYDROGENATION CATALYST

(71) Applicant: SABIC GLOBAL TECHNOLOGIES B.V., Bergen op Zoom (NL)

(72) Inventors: Naresh Dhachapally, Hyderabad (IN); Biju Maippan Devassy, Bangalore (IN); Nigit Jose Meleppuram, Bangalore (IN); Vinod Sankaran Nair, Bangalore (IN)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 220 days.

(21) Appl. No.: 18/720,861

(22) PCT Filed: Dec. 19, 2022

(86) PCT No.: PCT/IB2022/062489

§ 371 (c)(1),
(2) Date: Jun. 17, 2024

(87) PCT Pub. No.: WO2023/119131

PCT Pub. Date: Jun. 29, 2023

(65) Prior Publication Data

US 2025/0065309 A1 Feb. 27, 2025

(30) Foreign Application Priority Data

Dec. 22, 2021 (EP) ..................................... 21217107

(51) Int. Cl.
*B01J 23/63* (2006.01)
*B01J 21/04* (2006.01)
(Continued)

(52) U.S. Cl.
CPC ............... *B01J 23/63* (2013.01); *B01J 21/04* (2013.01); *B01J 21/12* (2013.01); *B01J 37/0213* (2013.01);
(Continued)

(58) Field of Classification Search
CPC ... B01J 23/63; B01J 21/04; B01J 21/12; B01J 137/0213; B01J 137/0236; B01J 35/40;
(Continued)

(56) References Cited

U.S. PATENT DOCUMENTS

| | | | |
|---|---|---|---|
| 7,235,706 B2 | 6/2007 | Iezzi et al. | |
| 9,776,170 B2 | 10/2017 | Kaminsky et al. | |

(Continued)

FOREIGN PATENT DOCUMENTS

| | | |
|---|---|---|
| CN | 104971717 A | 10/2015 |
| CN | 108114717 A | 6/2018 |

(Continued)

OTHER PUBLICATIONS

Extended European Search Report, EP Application No. 21217107.8-1101, dated Jun. 24, 2022, 10 pages.

(Continued)

*Primary Examiner* — Kyle Armstrong
(74) *Attorney, Agent, or Firm* — CANTOR COLBURN LLP

(57) ABSTRACT

An alkane dehydrogenation catalyst including a support; and on the support, an active layer including gallium oxide, aluminum oxide, cerium oxide, a Group 1 metal oxide, and a Group 8-11 metal oxide. The catalyst composition of the examples comprises oxides of gallium, cerium, potassium, platinum and aluminium.

15 Claims, 7 Drawing Sheets

(51) Int. Cl.

| | |
|---|---|
| *B01J 21/12* | (2006.01) |
| *B01J 37/02* | (2006.01) |
| *B01J 37/08* | (2006.01) |
| *C07C 5/32* | (2006.01) |
| *B01J 35/40* | (2024.01) |

(52) U.S. Cl.
CPC ........... *B01J 37/0236* (2013.01); *B01J 37/08* (2013.01); *C07C 5/322* (2013.01); *B01J 35/40* (2024.01); *C07C 2521/04* (2013.01); *C07C 2523/08* (2013.01); *C07C 2523/10* (2013.01)

(58) Field of Classification Search
CPC . C07C 5/322; C07C 2521/04; C07C 2523/08; C07C 2523/10
See application file for complete search history.

(56) References Cited

U.S. PATENT DOCUMENTS

| | | | | |
|---|---|---|---|---|
| 9,884,314 | B2 | 2/2018 | Luo et al. | |
| 10,933,405 | B2* | 3/2021 | Fridman | .................. B01J 23/63 |

| | | | | | |
|---|---|---|---|---|---|
| 2008/0051617 | A1* | 2/2008 | Sangar | ...................... C07C 2/76 585/403 |
| 2020/0223767 | A1* | 7/2020 | Xing | ........................ B01J 23/10 |

FOREIGN PATENT DOCUMENTS

| | | | |
|---|---|---|---|
| CN | 112221493 | A | 1/2021 |
| EP | 3083038 | B1 | 3/2021 |
| WO | 2019011660 | A1 | 1/2019 |
| WO | 2019115627 | A1 | 6/2019 |
| WO | WO-2019147424 | A1 * | 8/2019 ........... C07C 5/3332 |
| WO | 2021250612 | A1 | 12/2021 |

OTHER PUBLICATIONS

International Search Report, International Application No. PCT/IB2022/062489, Filing Date Dec. 19, 2022, Date of Mailing Apr. 12, 2023, 5 pages.

Written Opinion, International Application No. PCT/IB2022/062489, Filing Date Dec. 19, 2022, Date of Mailing Apr. 12, 2023, 9 pages.

\* cited by examiner

ALKANE DEHYDROGENATION CATALYST

CROSS REFERENCE TO RELATED APPLICATION

This application is a National Stage application of PCT/IB2022/062489, filed Dec. 19, 2022, which claims the benefit of and priority to European Application 21217107.8, filed on Dec. 22, 2021, the content of both of which are incorporated by reference in their entirety.

BACKGROUND

Alkane dehydrogenation is used for producing a variety of alkene products. An example of an alkene product that may be produced by alkane dehydrogenation is isobutylene, which may be used for producing methyl tert-butyl ether. Alkane dehydrogenation may be conducted in a fixed bed reactor with various types of catalysts.

As described above, conventional practice provides for alkane dehydrogenation to produce a variety of alkene products. While processes and catalysts for alkane dehydrogenation exist, opportunities for improvement in alkane conversion exist and are addressed by the improvements to gallium oxide-based catalyst of the present disclosure. Accordingly, disclosed, in various embodiments are processes and methods for creating a dehydrogenation catalyst and processes of dehydrogenating an alkane that have been discovered. The disclosed processes may advantageously provide for improved alkane conversion.

BRIEF DESCRIPTION

As described above, conventional practice provides for use of gallium-based catalysts in alkane dehydrogenation processes. However, gallium-based alkane dehydrogenation catalysts may not perform as well as known chromium-based dehydrogenation catalysts. Because of potential environmental and health-related issues which may arise when using chromium-based catalyst, there is a need to use non-chromium-based catalysts with similar performance characteristics. Thus, while catalysts for alkane dehydrogenation exist, opportunities for improvement exist and are addressed by the catalysts, processes, and methods of the present disclosure. A solution to address the deficiencies of conventional alkane dehydrogenation catalysts has been discovered. Accordingly, disclosed, in various embodiments, are alkane dehydrogenation catalysts, methods of forming an alkane dehydrogenation catalyst, and processes of dehydrogenating an alkane. The disclosed alkane dehydrogenation catalyst may not include chromium and may advantageously provide for improved alkane conversion.

Disclosed herein is an alkane dehydrogenation catalyst including a support; and on the support, an active layer including gallium oxide, aluminum oxide, cerium oxide, a Group 1 metal oxide, and a Group 8-11 metal oxide.

Disclosed herein is a method of forming an alkane dehydrogenation catalyst, the method including forming an impregnation solution including a gallium precursor, an aluminum precursor, a cerium precursor, a Group 1 metal precursor, and a Group 8-11 metal precursor; contacting the impregnation solution with a catalyst support material to deposit gallium, aluminum, cerium, the Group 1 metal, and the Group 8-11 metal on the catalyst support material and form an impregnated support; drying the impregnated support to form a dried impregnated support; and calcining the dried impregnated support to form the alkane dehydrogenation catalyst.

Disclosed herein is a process of dehydrogenating an alkane, the process including obtaining a catalyst including a support, and on the support, an active layer including gallium oxide, aluminum oxide, cerium oxide, a Group 1 metal oxide, and a Group 8-11 metal oxide; and contacting the alkane dehydrogenation catalyst with a feed including the alkane at a temperature of 450 to 800° C., or 500 to 750° C., to produce a product stream including an alkene.

The above described and other features are exemplified by the following figures and detailed description.

Any combination or permutation of embodiments is envisioned. Additional advantageous features, functions and applications of the disclosed catalysts, processes, and methods of the present disclosure will be apparent from the description which follows, particularly when read in conjunction with the appended figures.

BRIEF DESCRIPTION OF THE DRAWINGS

The following figures are exemplary embodiments.

Exemplary embodiments of the present disclosure are further described with reference to the appended figures. It is to be noted that the various features, steps, and combinations of features/steps described below can be arranged and organized differently to result in embodiments which are still within the scope of the present disclosure. To assist those of ordinary skill in the art in making, using, and practicing the disclosed catalysts, methods, and processes, reference is made to the appended figures, wherein.

DETAILED DESCRIPTION

Figure 1:
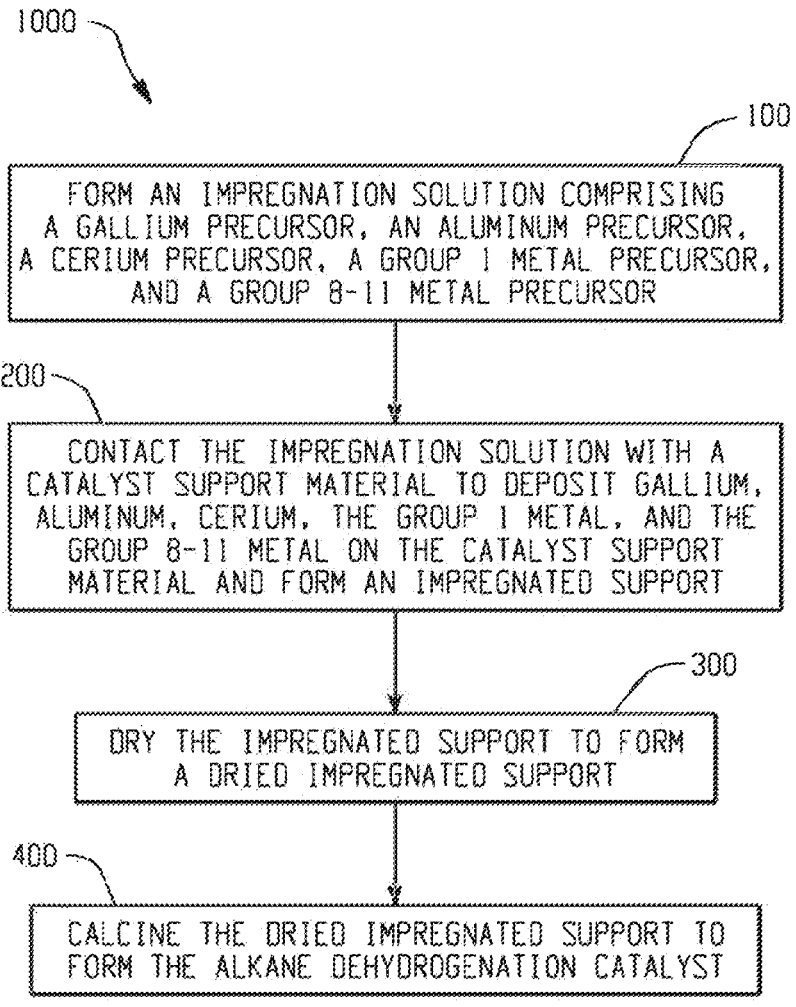
FIG. 1 illustrates a flowchart of a method of forming an alkane dehydrogenation catalyst.

The exemplary embodiments disclosed herein are illustrative of advantageous alkane dehydrogenation catalysts, methods of forming an alkane dehydrogenation catalyst, and processes of dehydrogenating an alkane. It should be understood, however, that the disclosed embodiments are merely exemplary of the present disclosure, which may be embodied in various forms. Therefore, details disclosed herein with reference to exemplary catalysts, methods, and processes are not to be interpreted as limiting, but merely as the basis for teaching one skilled in the art the advantageous catalysts, methods, and processes of the present disclosure.

In an embodiment, an alkane dehydrogenation catalyst includes a support; and on the support, an active layer including gallium oxide, aluminum oxide, cerium oxide, a Group 1 metal oxide, and a Group 8-11 metal oxide. As used herein, the active material and the components thereof being "on a support" or "on the support" refers to the active material and the components thereof being separate components from the support. Accordingly, each of the components of the active layer, i.e., gallium oxide, aluminum oxide, cerium oxide, a Group 1 metal oxide, and a Group 8-11 metal oxide, is distinct from the support, though a composition of one or more components of the active layer (e.g., aluminum oxide) may be the same as a composition of the support (e.g., alumina).

While not wanting to be bound by theory, it is understood that the various components of the active layer contribute to desirable improved alkane conversion, for example, of isobutane to isobutylene. For example, the presence of aluminum oxide in the active layer, in addition to and separate from alumina of the support, contributes to improved alkane conversion.

The support may include alumina. The support may include silica-modified alumina. With further reference to the definition herein of "on a support" or "on the support," the aluminum oxide of the active layer, which is on the support, is a separate, distinct component from the alumina of the support. As will be described in further detail herein, the active layer, and the aluminum oxide thereof, is deposited on the support.

The active layer may include, based on a total weight of the alkane dehydrogenation catalyst, 0.1 to 4.0 weight percent, or 0.2 to 3.5 weight percent, of the gallium oxide, 1 to 10 weight percent, or 2 to 8 weight percent, of the aluminum oxide, 0.1 to 3 weight percent, or 0.2 to 2.5 weight percent, of the cerium oxide, 0.1 to 2 weight percent, or 0.2 to 1.5 weight percent, of the Group 1 metal oxide, and 0.001 to 0.03 weight percent, or 0.002 to 0.02 weight percent, of the Group 8-11 metal oxide. In an embodiment, a molar ratio of gallium to aluminum in the active layer is less than 0.5:1, or within a range of 0.01:1 to less than 0.5:1, 0.05 to 0.4, or 0.1 to 0.3. The Group 8-11 metal oxide may include a Group 10 metal. The Group 8-11 metal oxide may include platinum. The Group 1 metal oxide may include potassium, sodium, cesium, or a combination thereof.

In an embodiment, the alkane dehydrogenation catalyst has a surface area in a range of 50 to 250 square meters per gram (m²/g), or 75 to 225 m²/g or 100 to 200 m²/g. The pore volume (nitrogen adsorption-desorption) of the alkane dehydrogenation catalyst may be in a range of 0.1 to 0.9 cubic meters per gram (cm³/g), or 0.2 to 0.8 cm³/g or 0.3 to 0.7 cm³/g. In an embodiment, the alkane dehydrogenation catalyst has a bulk density in a range of 0.5 to 1.2 grams per milliliter (g/ml), or 0.55 to 1 g/ml or 0.6 to 0.8 g/ml. In an embodiment, the alkane dehydrogenation catalyst has a crush strength greater than or equal to about 1 dekanewtons per millimeter (daN/mm).

In an embodiment, with reference to FIG. 1, a method of forming an alkane dehydrogenation catalyst (1000) includes forming an impregnation solution including a gallium precursor, an aluminum precursor, a cerium precursor, a Group 1 metal precursor, and a Group 8-11 metal precursor (100); contacting the impregnation solution with a catalyst support material to deposit gallium, aluminum, cerium, the Group 1 metal, and the Group 8-11 metal on the catalyst support material and form an impregnated support (200); drying the impregnated support to form a dried impregnated support (300); and calcining the dried impregnated support to form the alkane dehydrogenation catalyst (400).

The gallium precursor may include a gallium nitrate, the aluminum precursor may include an aluminum nitrate, the cerium precursor may include a cerium nitrate, the Group 1 metal precursor may include a Group 1 metal nitrate, and the Group 8-11 metal precursor may include a Group 8-11 nitrate. In an embodiment, the support includes alumina or silica-modified alumina, the Group 1 metal oxide includes potassium, and the Group 8-11 metal oxide includes platinum.

The support material may be in various forms (e.g., tablets, lobes, spheres, extrudates, etc.). By way of example, the support material may be shaped into cylindrical tablets (opened or closed) by direct compression using tableting methodology. The raw materials used to generate the support material may be mixed with a binder (e.g., an acid such as steric acid), a lubricant (e.g., graphite), or a combination thereof to form the support material. The support material may be shaped in the form of trilobes or quadrilobes using extrusion molding techniques. By way of example, a carrier may be mixed with solvent (e.g., water or alcohol), binder (e.g., starch, cellulose, etc.), and a surface tension modifier to form a paste that may flow freely through the die of an extruder to form an extrudate. In an embodiment, the alkane dehydrogenation catalyst is in the form of an extrudate having a diameter of 1 to 4 millimeters, or 2 to 3.5 millimeters, and a length of 2 to 10 millimeters, or 3 to 9 millimeters.

In an embodiment, forming the alkane dehydrogenation catalyst includes contacting an aqueous solution including precursors of the catalytic metals of the active layer with a porous support (e.g., alumina-silica) by incipient wetness impregnation (also called capillary impregnation or dry impregnation). With incipient wetness impregnation, capillary action draws the solution into the pores, and thus an amount of the aqueous solution added to the support is typically equal to or less than the total pore volume of the support. If the amount of aqueous solution added to the support is less than the total pore volume of the support, multiple contacting steps may be used such that the total amount of aqueous solution added to the support is about equal to the total pore volume of the support. The aqueous solution added in excess of the support pore volume may cause the solution transport to change from a capillary action process to a diffusion process, which may slow the impregnation process. The loading of the aqueous solution may be controlled by the concentration of metal ions in solution, which means that the support external surface does not play an important role, but merely acts as a physical support. The maximum loading of the aqueous solution into the support may be limited by the solubility of the individual components of the aqueous solution in the solution (e.g., in water). The impregnated support may then be dried and calcined to drive off the volatile components within the solution, depositing the catalytic metals on the external surface of the support (e.g., outer surface and surface of pores). The catalytic metal precursors may include, for example, a nitrate, an oxide, a hydroxide, a chloride, an acetate, a carbonate, or a combination thereof.

In an embodiment, a temperature of the drying is in a range of 70 to 150° C., or 80 to 140° C. or 90 to 130° C. In an embodiment, the calcining converts the precursors to oxides. In an embodiment, the calcination temperature is in a range of 500 to 1,000° C., or 600 to 975° C. or 700 to 950° C. A temperature ramp (i.e., a heating rate) of the calcining may be in a range of 0.5 to 10° C./minute (min), or 1 to 9° C./min or 2 to 8° C./min. In an embodiment, the calcination duration is in a range of 0.5 to 10 hours, or 1 to 7 hours or 1.5 to 5 hours. In an embodiment, the calcining is performed in an atmospheric environment of air, including, for example, nitrogen, oxygen, carbon dioxide, and water vapor.

In an embodiment, a process of dehydrogenating an alkane includes obtaining a catalyst including a support, and on the support, an active layer including gallium oxide, aluminum oxide, cerium oxide, a Group 1 metal oxide, and a Group 8-11 metal oxide; and contacting the alkane dehydrogenation catalyst with a feed including the alkane at a temperature of 450 to 800° C., or 500 to 750° C., to produce a product stream including an alkene.

In an embodiment, the alkane dehydrogenation is conducted in a fixed bed reactor. The reaction conditions may further include a reaction pressure of 0.2 to 1 bar, or 0.3 to 0.9 bar, or 0.4 to 0.8 bar. The reaction conditions may further include a gas hourly space velocity of 300 to 800 ml $h^{-1}$ $g^{-1}$, or 400 to 750 ml $h^{-1}$ $g^{-1}$, 500 to 700 ml $h^{-1}$ $g^{-1}$.

The process of dehydrogenating the alkane may further include oxidation followed by alkane dehydrogenation. In an embodiment, the oxidation and the dehydrogenation are cyclically repeated. An inert gas such as nitrogen may be passed through the reactor between the oxidation and dehydrogenation steps.

This disclosure is further illustrated by the following examples, which are non-limiting.

EXAMPLES

Comparative Example 1

Catalyst was prepared by co-impregnation. Alumina extrudates used for the impregnation were prepared using the following procedure. Boehmite (PBA M05, Chika Pvt. Ltd.) material was extruded using nitric acid as a peptizing agent. To 36 milliliters (ml) of 70 weight percent (wt. %) nitric acid, water was added to make 500 ml of solution. The nitric acid solution (300 ml) was added dropwise to boehmite powder (500 grams (g)) and the mixture was mixed for about 30 minutes. The obtained dough was then extruded using a lab extruder (Sunsai), using a die with 3.5 millimeter (mm) circular openings. The prepared wet extrudates were dried at 120° C. for 16 hours in air in an oven. The dried extrudates (160 g) were calcined at 750° C. for 4 hours in a muffle furnace with a heating rate of 5 degrees Celsius per minute (° C./min) and an air flow rate of 480±10 milliliters per minute (ml/min). The obtained alumina ($\gamma$-$Al_2O_3$) extrudates (size: about 3 mm diameter and about 6-8 mm length) were used for catalyst preparation. The alumina extrudate support (about 100 g) was heat treated in an oven at 120° C. for 16 hours in the presence of air to remove moisture. The dried alumina extrudate support after cooling to room temperature was used for catalyst preparation by an incipient wetness impregnation method. Gallium nitrate hexahydrate ($Ga(NO_3)_3 \cdot 6H_2O$, Sigma-Aldrich), tetraamineplatinum nitrate ($Pt(NH_3)_4(NO_3)_2$, Sigma-Aldrich), cerium nitrate hexahydrate ($Ce(NO_3)_3 \cdot 6H_2O$, Sigma-Aldrich), and potassium nitrate ($KNO_3$, Sigma-Aldrich) materials were used as precursors of gallium, platinum, cerium, and potassium, respectively.

The catalyst was prepared by incipient wetness impregnation of the support with an aqueous clear solution prepared by dissolving 5.458 g of gallium nitrate hexahydrate, 0.66 ml of 1.5% tetraamineplatinum nitrate solution (1.5 g/100 ml solution), 1.586 g of cerium nitrate hexahydrate, and 1.073 g potassium nitrate in water to make a 43.7 ml (based on pore volume 0.45 milliliters per gram (ml/g)) solution. The impregnation was carried out by contacting the prepared impregnation solution with the alumina extrudate support (97.29 g) at room temperature. The impregnated alumina support was then kept at room temperature for 12 hours and then dried at 120° C. for 16 hours. The dried sample was then calcined at 800° C. for 2 hours with a heating rate of 5° C./min in the presence of air (flow rate, 8 milliliters per gram per minute (ml $g^{-1}$ $min^{-1}$)) in a down flow tubular reactor. After calcination, the catalyst was cooled in the presence of air, stored in an airtight container, and used for an isobutane dehydrogenation reaction. The final calculated composition of the catalyst is given in Table 1.

Comparative Example 2

Catalyst was prepared by co-impregnation. Alumina extrudates used for the impregnation were prepared using the following procedure. Boehmite (PBA M05, Chika Pvt. Ltd.) material was extruded using nitric acid as a peptizing agent. To 36 ml of 70 wt. % nitric acid, water was added to make 500 ml of solution. The nitric acid solution (300 ml) was added dropwise to boehmite powder (500 g) and the mixture was mixed for about 30 minutes. The obtained dough was then extruded using a lab extruder (Sunsai), using a die with 3.5 mm circular openings. The prepared wet extrudates were dried at 120° C. for 16 hours in air in an oven. The dried extrudates (160 g) were calcined at 750° C. for 4 hours in a muffle furnace with a heating rate of 5° C./min and an air flow rate of 480±10 ml/min. The obtained alumina ($\gamma$-$Al_2O_3$) extrudates (size: about 3 mm diameter and about 6-8 mm length) were used for catalyst preparation. The alumina extrudate support (about 100 g) was heat treated in an oven at 120° C. for 16 hours in the presence of air to remove moisture. The dried alumina extrudate support after cooling to room temperature was used for catalyst preparation by an incipient wetness impregnation method. Gallium nitrate hexahydrate ($Ga(NO_3)_3 \cdot 6H_2O$, Sigma-Aldrich), tetraamineplatinum nitrate ($Pt(NH_3)_4(NO_3)_2$, Sigma-Aldrich), potassium nitrate ($KNO_3$, Sigma-Aldrich), and aluminum nitrate nonahydrate ($Al(NO_3)_3 \cdot 9H_2O$, Sigma-Aldrich) materials were used as precursors of gallium, platinum, potassium and aluminum, respectively.

The catalyst was prepared by incipient wetness impregnation of the support with an aqueous clear solution prepared by dissolving 5.457 g of gallium nitrate hexahydrate, 0.66 ml of 1.5% tetraamineplatinum nitrate solution (1.5 g/100 ml solution), 1.073 g potassium nitrate, and 36.79 g of aluminum nitrate nonahydrate in water to make a 41.8 ml (based on pore volume 0.45 ml/g) solution. The impregnation was carried out by contacting the prepared impregnation solution with the alumina extrudate support (92.89 g) at room temperature. The impregnated alumina support was then kept at room temperature for 12 hours and then dried at 120° C. for 16 hours. The dried sample was then calcined at 800° C. for 2 hours with a heating rate of 5° C./min in the presence of air (flow rate, 8 ml $g^{-1}$ $min^{-1}$) in a down flow tubular reactor. After calcination, the catalyst was cooled in the presence of air, stored in an airtight container, and used for an isobutane dehydrogenation reaction. The final calculated composition of the catalyst is given in Table 1.

Example 1

Catalyst was prepared by co-impregnation. Alumina extrudates used for the impregnation were prepared using the following procedure. Boehmite (PBA M05, Chika Pvt. Ltd.) material was extruded using nitric acid as a peptizing agent. To 36 ml of 70 wt. % nitric acid, water was added to make 500 ml of solution. The nitric acid solution (300 ml) was added dropwise to boehmite powder (500 g) and the mixture was mixed for about 30 minutes. The obtained dough was then extruded using a lab extruder (Sunsai), using a die with 3.5 mm circular openings. The prepared wet extrudates were dried at 120° C. for 16 hours in air in an oven. The dried extrudates (160 g) were calcined at 750° C. for 4 hours in a muffle furnace with a heating rate of 5° C./min and an air flow rate of 480±10 ml/min. The obtained alumina ($\gamma$-$Al_2O_3$) extrudates (size: about 3 mm diameter and about 6-8 mm length) were used for catalyst preparation. The alumina extrudate support (about 100 g) was heat treated in an oven at 120° C. for 16 hours in the presence of air to remove moisture. The dried alumina extrudate support after cooling to room temperature was used for catalyst preparation by an incipient wetness impregnation method. Gallium nitrate hexahydrate ($Ga(NO_3)_3 \cdot 6H_2O$, Sigma-Aldrich), tetraamineplatinum nitrate ($Pt(NH_3)_4(NO_3)_2$, Sigma-Aldrich), cerium nitrate hexahydrate ($Ce(NO_3)_3 \cdot 6H_2O$, Sigma-Aldrich), potassium nitrate ($KNO_3$, Sigma-Aldrich), and aluminum nitrate nonahydrate ($Al(NO_3)_3 \cdot 9H_2O$, Sigma-Aldrich) materials were used as precursors of gallium, platinum, cerium, potassium, and aluminum, respectively.

The catalyst was prepared by incipient wetness impregnation of the support with an aqueous clear solution prepared by dissolving 5.457 g of gallium nitrate hexahydrate, 0.66 ml of 1.5% tetraamineplatinum nitrate solution (1.5 g/100 ml solution), 1.534 g of cerium nitrate hexahydrate, 1.073 g potassium nitrate and 36.79 g of aluminum nitrate nonahydrate in water to make a 41.53 ml (based on pore volume 0.45 ml/g) solution. The impregnation was carried out by contacting the prepared impregnation solution with the alumina extrudate support (92.29 g) at room temperature. The impregnated alumina support was then kept at room temperature for 12 hours and then dried at 120° C. for 16 hours. The dried sample was then calcined at 800° C. for 2 hours with a heating rate of 5° C./min in the presence of air (flow rate, 8 ml g$^{-1}$ min$^{-1}$) in a down flow tubular reactor. After calcination, the catalyst was cooled in the presence of air, stored in an airtight container, and used for an isobutane dehydrogenation reaction. The final calculated composition of the catalyst is given in Table 1.

Example 2

Catalyst was prepared by co-impregnation. Alumina extrudates used for the impregnation were prepared using the following procedure. Boehmite (PBA M05, Chika Pvt. Ltd.) material was extruded using nitric acid as a peptizing agent. To 36 ml of 70 wt. % nitric acid, water was added to make 500 ml of solution. The nitric acid solution (300 ml) was added dropwise to boehmite powder (500 g) and the mixture was mixed for about 30 minutes. The obtained dough was then extruded using a lab extruder (Sunsai), using a die with 3.5 mm circular openings. The prepared wet extrudates were dried at 120° C. for 16 hours in air in an oven. The dried extrudates (160 g) were calcined at 750° C. for 4 hours in a muffle furnace with a heating rate of 5° C./min and an air flow rate of 480±10 ml/min. The obtained alumina ($\gamma$-$Al_2O_3$) extrudates (size: about 3 mm diameter and about 6-8 mm length) were used for catalyst preparation. The alumina extrudate support (about 100 g) was heat treated in an oven at 120° C. for 16 hours in the presence of air to remove moisture. The dried alumina extrudate support after cooling to room temperature was used for catalyst preparation by an incipient wetness impregnation method. Gallium nitrate hexahydrate ($Ga(NO_3)_3 \cdot 6H_2O$, Sigma-Aldrich), tetraamineplatinum nitrate ($Pt(NH_3)_4(NO_3)_2$, Sigma-Aldrich), cerium nitrate hexahydrate ($Ce(NO_3)_3 \cdot 6H_2O$, Sigma-Aldrich), potassium nitrate ($KNO_3$, Sigma-Aldrich) and aluminum nitrate nonahydrate ($Al(NO_3)_3 \cdot 9H_2O$, Sigma-Aldrich) materials were used as precursors of gallium, platinum, cerium, potassium and aluminum, respectively.

The catalyst was prepared by incipient wetness impregnation of the support with an aqueous clear solution prepared by dissolving 10.915 g of gallium nitrate hexahydrate, 1.32 ml of 1.5% tetraamineplatinum nitrate solution (1.5 g/100 mL solution), 3.069 g of cerium nitrate hexahydrate, 1.938 g potassium nitrate and 36.79 g of aluminum nitrate nonahydrate in water to make a 40.6 ml (based on pore volume 0.45 ml/g) solution. The impregnation was carried out by contacting the prepared impregnation solution with the alumina extrudate support (90.08 g) at room temperature. The impregnated alumina support was then kept at room temperature for 12 hours and then dried at 120° C. for 16 hours. The dried sample was then calcined at 800° C. for 2 hours with a heating rate of 5° C./min in the presence of air (flow rate, 8 ml g$^{-1}$ min$^{-1}$) in a down flow tubular reactor. After calcination, the catalyst was cooled in the presence of air, stored in an airtight container, and used for an isobutane dehydrogenation reaction. The final calculated composition of the catalyst is given in Table 1.

Example 3

Catalyst was prepared by co-impregnation. Alumina extrudates used for the impregnation were prepared using the following procedure. Boehmite (PBA M05, Chika Pvt. Ltd.) material was extruded using nitric acid as a peptizing agent. To 36 ml of 70 wt. % nitric acid, water was added to make 500 ml of solution. The nitric acid solution (300 ml) was added dropwise to boehmite powder (500 g) and the mixture was mixed for about 30 minutes. The obtained dough was then extruded using a lab extruder (Sunsai), using a die with 3.5 mm circular openings. The prepared wet extrudates were dried at 120° C. for 16 hours in air in an oven. The dried extrudates (160 g) were calcined at 900° C. for 10 hours in a muffle furnace with a heating rate of 5° C./min and an air flow rate of 480±10 ml/min. The obtained alumina (combination of $\delta$- and $\theta$-$Al_2O_3$) extrudates (size: about 3 mm diameter and about 6-8 mm length) were used for catalyst preparation. The alumina extrudate support (about 100 g) was heat treated in an oven at 120° C. for 16 hours in the presence of air to remove moisture. The dried alumina extrudate support after cooling to room temperature was used for catalyst preparation by an incipient wetness impregnation method. Gallium nitrate hexahydrate ($Ga(NO_3)_3 \cdot 6H_2O$, Sigma-Aldrich), tetraamineplatinum nitrate ($Pt(NH_3)_4(NO_3)_2$, Sigma-Aldrich), cerium nitrate hexahydrate ($Ce(NO_3)_3 \cdot 6H_2O$, Sigma-Aldrich), potassium nitrate ($KNO_3$, Sigma-Aldrich), and aluminum nitrate nonahydrate ($Al(NO_3)_3 \cdot 9H_2O$, Sigma-Aldrich) materials were used as precursors of gallium, platinum, cerium, potassium, and aluminum, respectively.

The catalyst was prepared by incipient wetness impregnation of the support with an aqueous clear solution prepared by dissolving 5.457 g of gallium nitrate hexahydrate, 0.66 ml of 1.5% tetraamineplatinum nitrate solution (1.5 g/100 ml solution), 1.534 g of cerium nitrate hexahydrate, 1.073 g potassium nitrate and 36.79 g of aluminum nitrate nonahydrate in water to make a 30 ml (based on pore volume 0.33 ml/g) solution. The impregnation was carried out by contacting the prepared impregnation solution with the alumina (combination of δ- and κ-Al₂O₃) extrudate support (92.29 g) at room temperature. The impregnated alumina support was then kept at room temperature for 12 hours and then dried at 120° C. for 16 hours. The dried sample was then calcined at 800° C. for 2 hours with a heating rate of 5° C./min in the presence of air (flow rate, 8 ml g⁻¹ min⁻¹) in a down flow tubular reactor. After calcination, the catalyst was cooled in the presence of air, stored in an airtight container, and used for an isobutane dehydrogenation reaction. The final calculated composition of the catalyst is given in Table 1.

Example 4

Catalyst was prepared by co-impregnation. The silica-modified alumina (1 wt. % SiO₂) was prepared using the following procedure. Boehmite (PBA M05, Chika Pvt. Ltd.) material was extruded using nitric acid as a peptizing agent.

pared by dissolving 5.457 g of gallium nitrate hexahydrate, 0.66 ml of 1.5% tetraamineplatinum nitrate solution (1.5 g/100 ml solution), 1.534 g of cerium nitrate hexahydrate, 1.073 g potassium nitrate and 36.79 g of aluminum nitrate nonahydrate in water to make a 41.53 ml (based on pore volume 0.45 ml/g) solution. The impregnation was carried out by contacting the prepared impregnation solution with the alumina extrudate support (92.29 g) at room temperature. The impregnated alumina support was then kept at room temperature for 12 hours and then dried at 120° C. for 16 hours. The dried sample was then calcined at 800° C. for 2 hours with a heating rate of 5° C./min in the presence of air (flow rate, 8 ml g⁻¹ min⁻¹) in a down flow tubular reactor. After calcination, the catalyst was cooled in the presence of air, stored in an airtight container, and used for an isobutane dehydrogenation reaction. The final calculated composition of the catalyst is given in Table 1. The weight percentage of each component is based on the total weight of the catalyst.

TABLE 1

|  | Ga₂O₃ (wt. %) | Ga (moles) | PtO₂ (wt. %) | K₂O (wt. %) | Al₂O₃ (wt. %) | Al (moles) | Ce₂O₃ (wt. %) | Ga:Al mole ratio | Support |
|---|---|---|---|---|---|---|---|---|---|
| Comparative Example 1 | 1.35 | — | 0.00675 | 0.5 | 0 | — | 0.6 | — | γ-Al₂O₃ |
| Comparative Example 2 | 1.35 | — | 0.00675 | 0.5 | 5 | — | 0 | — | γ-Al₂O₃ |
| Example 1 | 1.35 | 0.014 | 0.00675 | 0.5 | 5 | 2.646 | 0.6 | 0.147:1 | γ-Al₂O₃ |
| Example 2 | 2.7 | 0.029 | 0.01164 | 0.9 | 5 | 2.646 | 1.17 | 0.294:1 | γ-Al₂O₃ |
| Example 3 | 1.35 | 0.014 | 0.00675 | 0.5 | 5 | 2.646 | 0.6 | 0.147:1 | δ-/θ-Al₂O₃ |
| Example 4 | 1.35 | 0.014 | 0.00675 | 0.5 | 5 | 2.646 | 0.6 | 0.147:1 | γ-Al₂O₃ SiO₂ (1 wt. %) |

To 36 ml of 70 wt. % nitric acid added to water to make 500 ml of solution. To boehmite powder (500 g) was added dropwise 5% nitric acid (300 ml) containing silica sol (9.25 ml of silica sol (AS-40), Sigma-Aldrich) and the mixture was mixed for about 30 minutes. The obtained dough was then extruded using a lab extruder (Sunsai), the dies being 3.5 mm in diameter. The prepared wet extrudates were dried at 120° C. for 16 hours in air in an oven. The dried extrudates (160 g) were calcined at 750° C. for 4 hours in a muffle furnace with a heating rate of 5° C./min and airflow rate being 480±10 ml/min. The obtained extrudate (size: about 3 mm diameter and about 6-8 mm length) catalyst was used for catalyst preparation. The alumina (γ-Al₂O₃) extrudate support containing silica (about 100 g) was heat treated in an oven at 120° C. for 16 hours in the presence of air to remove moisture. The dried alumina extrudate support after cooling to room temperature was used for catalyst preparation by an incipient wetness impregnation method. Gallium nitrate hexahydrate (Ga(NO₃)₃·6H₂O, Sigma-Aldrich), tetraamineplatinum nitrate (Pt(NH₃)₄(NO₃)₂, Sigma-Aldrich), cerium nitrate hexahydrate (Ce(NO₃)₃·6H₂O, Sigma-Aldrich), potassium nitrate (KNO₃, Sigma-Aldrich) and aluminum nitrate nonahydrate (Al(NO₃)₃·9H₂O, Sigma-Aldrich) materials were used as precursors of gallium, platinum, cerium, potassium and aluminum, respectively.

The catalyst was prepared by incipient wetness impregnation of the support with an aqueous clear solution pre-

Catalyst Testing

The synthesized catalysts in extrudate form were loaded into a tubular fixed-bed quartz reactor. The details of the catalyst loading were as follows: catalyst weight=4.0 g, catalyst shape: extrudate (about 2.8 mm diameter and about 4-6 mm length), inert (quartz)) weight=6 g, inert shape=particles (size: 0.25-0.5 mm). The catalyst (extrudate) was weighed and loaded into the reactor and the voids were filled with inert material. A thermowell was placed in the middle of the catalyst bed. Above and below the catalyst bed, inert (size 1-1.4 mm) material was filled to maintain the temperature/reduce the flow-related mal-distribution.

After loading, the catalyst was used for the dehydrogenation reaction. Isobutane (99.9 volume percent (vol. %)) was used as the feed. A nitrogen purge separated the dehydrogenation and oxidation steps. The total isobutane feed flow in the dehydrogenation step corresponded to a gas hourly space velocity (GHSV) of 600 milliliters per hour per gram (ml h⁻¹ g⁻¹). The reactor outlet gases were analyzed by an online gas chromatograph (GC) (Agilent 6890, Agilent Scientific Instruments, USA) equipped with a flame ionization detector for hydrocarbon analysis and a thermal conductivity detector for hydrogen analysis. The reactant and products flow rates were measured using a Ritter type wet gas flow meter. The reactor was operated at about 0.5 bar partial pressure of isobutane by diluting the isobutane gas with N₂ gas in a 1:1 volume ratio. The reaction was carried in a cyclic mode with the following steps:

1. Oxidation in air at 650° C. for 10 minutes (min);
2. Cooling with nitrogen from 650 to 575° C. and hold for 20 min at 650° C. for temperature stabilization;
3. Start isobutane feed flow mixed with nitrogen (1:1) for dehydrogenation at 575° C. for 10 min;
4. GC analysis at the 9th minute from the start of the isobutane feed; and −5. Increase the temperature in nitrogen from 575 to 650° C. and hold for 5 min at 650° C. for temperature stabilization.

Steps 1-5 were repeated for 100 cycles.

Figure 2:
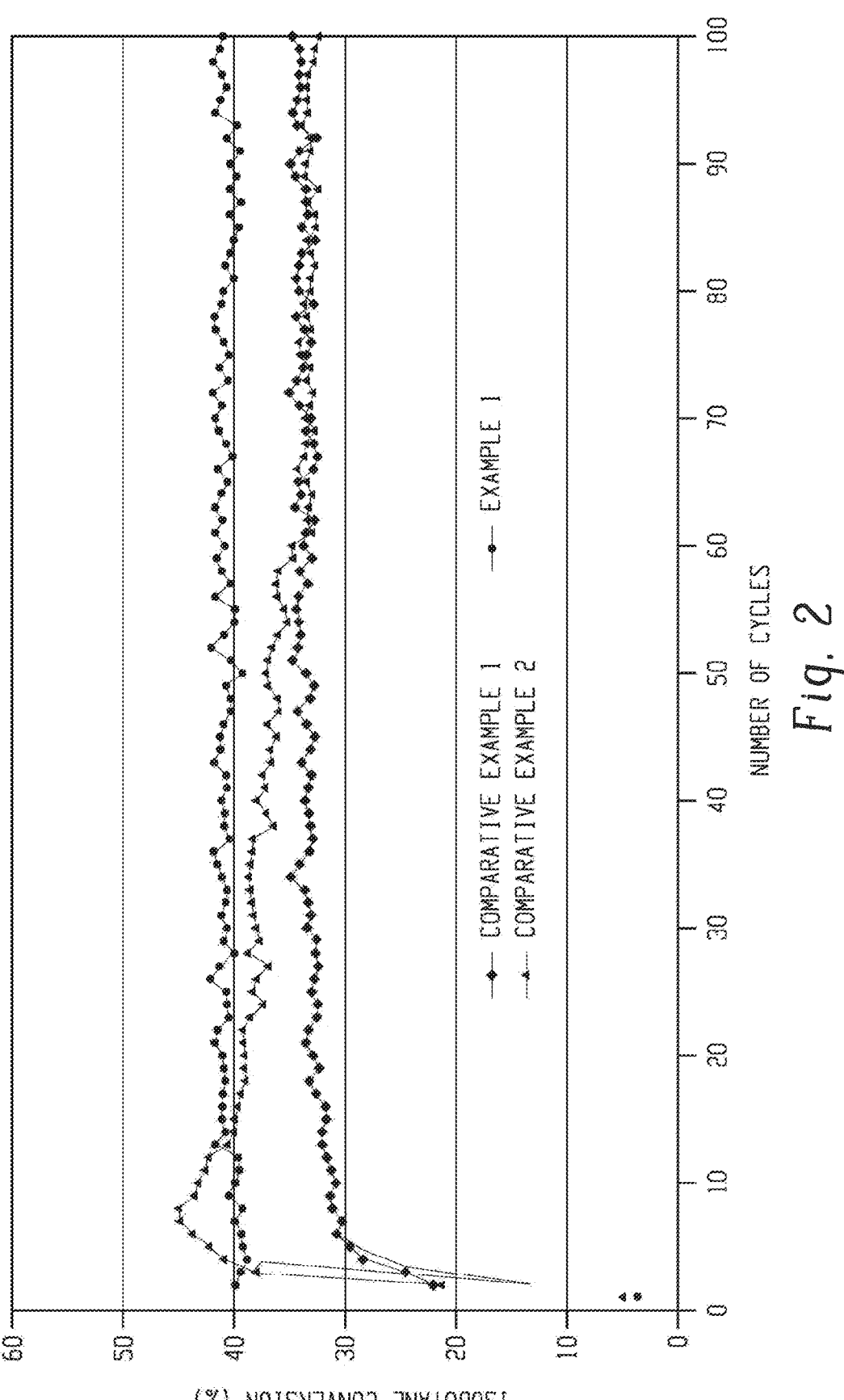
FIG. 2 is a graph of isobutane conversion (percent (%)) versus number of cycles of Comparative Examples 1 and 2 and Example 1.
Figure 3:
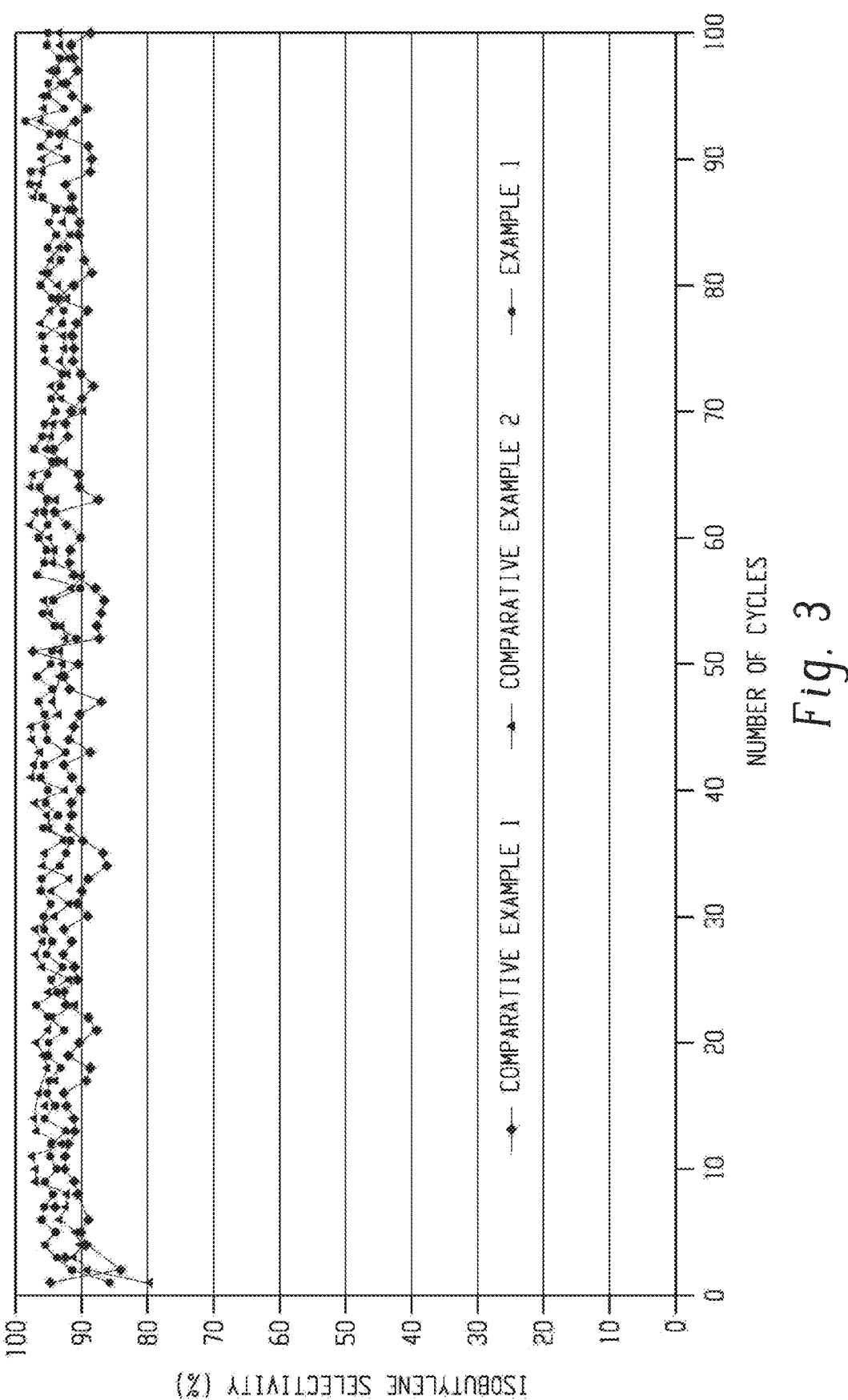
FIG. 3 is a graph of isobutylene selectivity (%) versus number of cycles of Comparative Examples 1 and 2 and Example 1.
Figure 4:
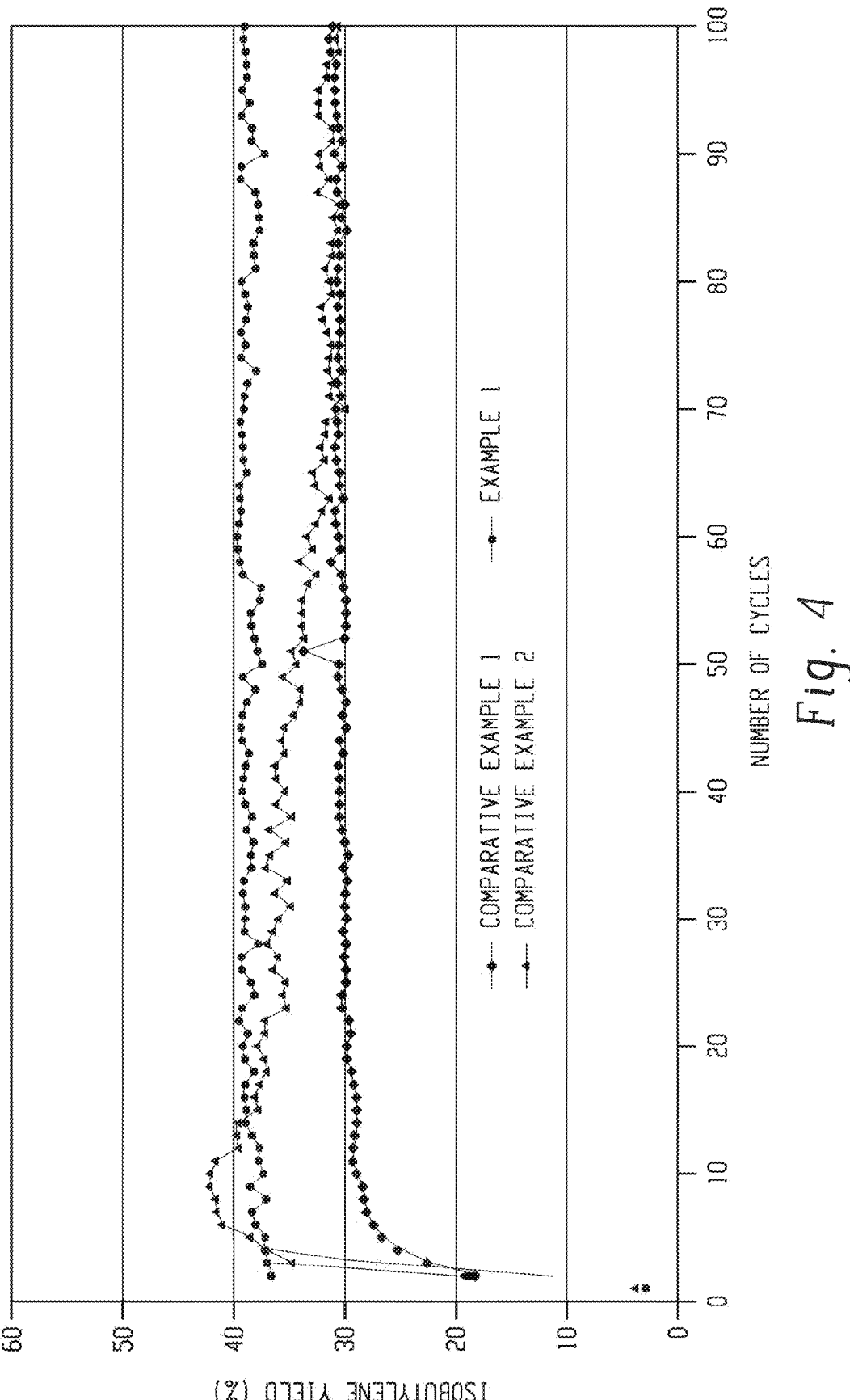
FIG. 4 is a graph of isobutylene yield (%) versus number of cycles of Comparative Examples 1 and 2 and Example 1.
Figure 5:
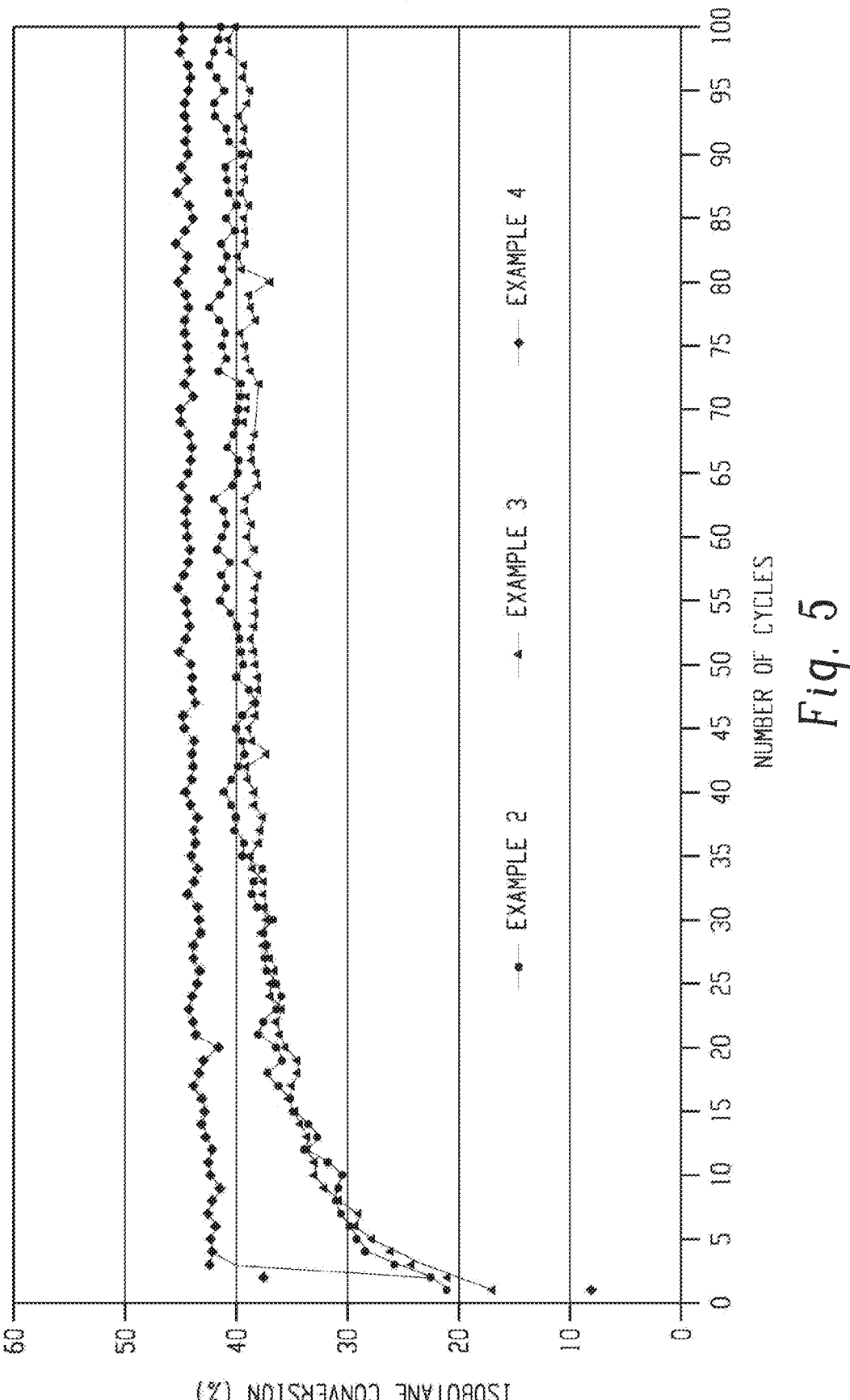
FIG. 5 is a graph of isobutane conversion (%) versus number of cycles of Examples 2-4.
Figure 6:
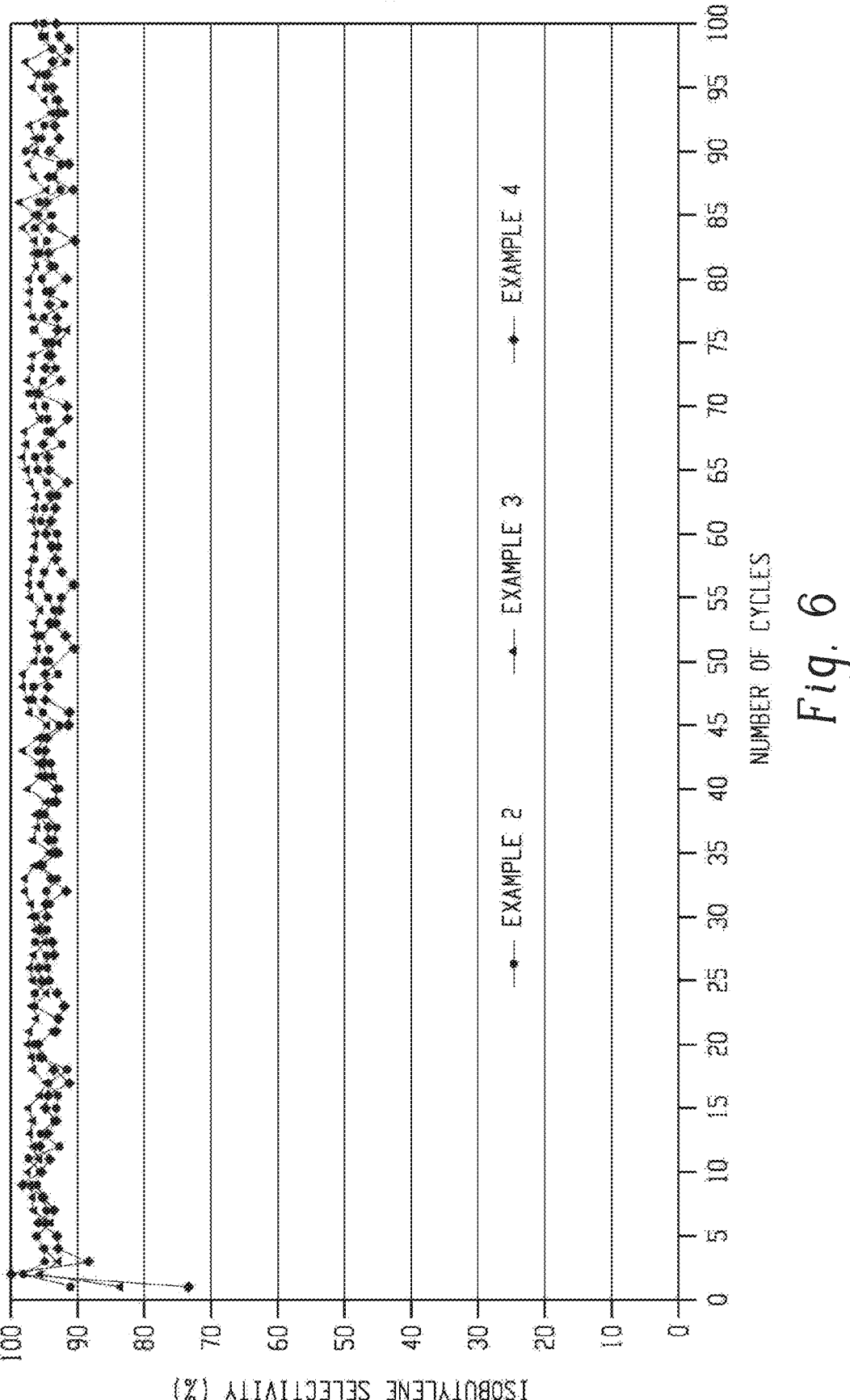
FIG. 6 is a graph of isobutylene selectivity (%) versus number of cycles of Examples 2-4.
Figure 7:
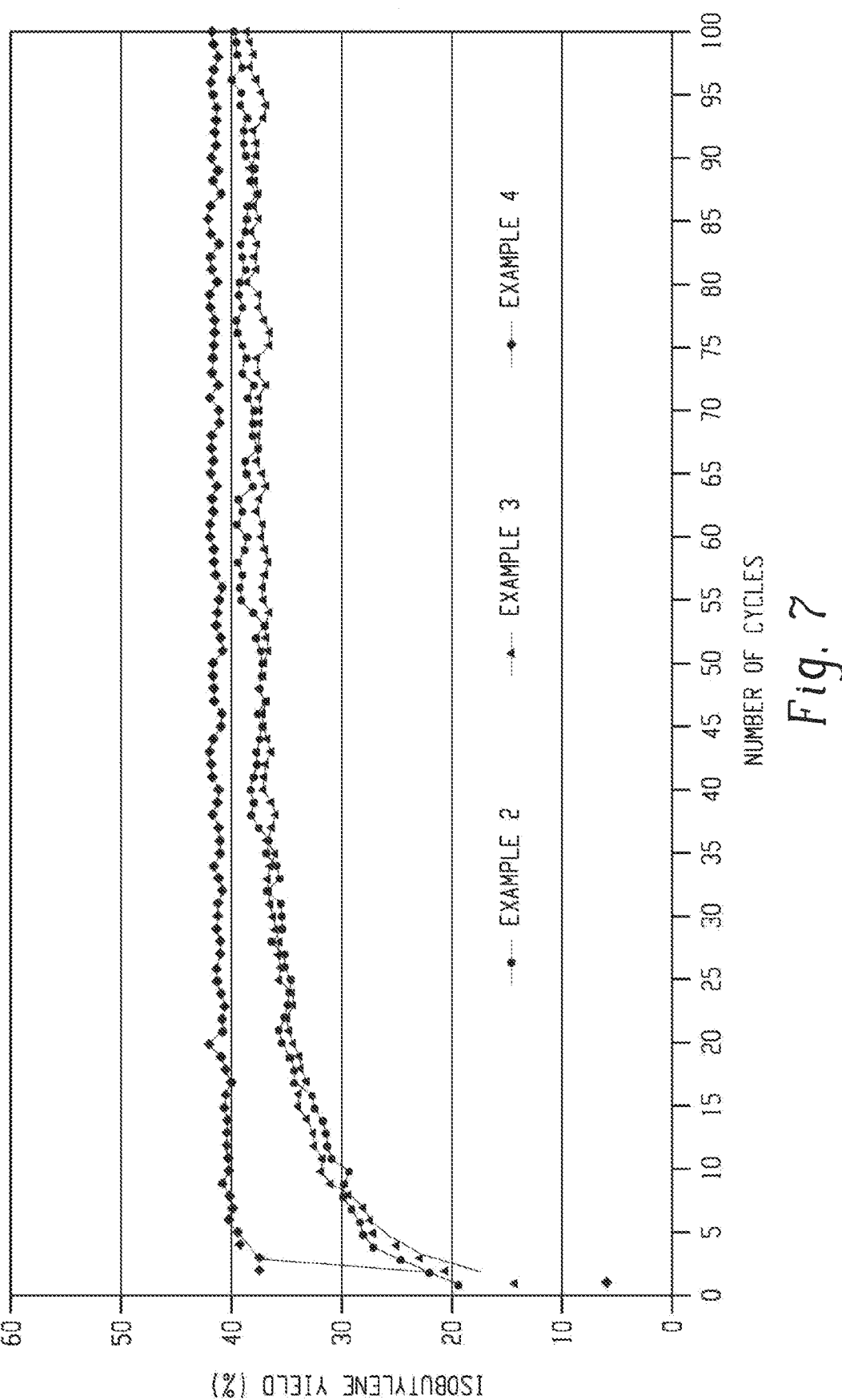
FIG. 7 is a graph of isobutylene yield (%) versus number of cycles of Examples 2-4.

The performance of the catalysts of Comparative Examples 1 and 2 and Example 1 is shown in FIGS. 2-4, the performance of the catalysts of Examples 2-4 is shown in FIGS. 5-7, and the average values of results after reaching steady state (81-100 cycles) are given in Table 2. The results show that the conversion increased for the catalysts containing an active layer including aluminum oxide, gallium oxide, a Group 1 metal oxide, a Group 8-11 metal oxide, and cerium oxide.

As used herein, the term "conversion" refers to the mole fraction (i.e., percent) of a reactant converted to a product or products. As used herein, the term "selectivity" refers to the mole fraction (i.e., percent) of reactant converted to a specified product, for example, isobutylene selectivity is the percentage of isobutane that was converted to isobutylene. As used herein, the term "yield" refers to the mole fraction (i.e., percent) of a specified product in a total product stream.

TABLE 2

| Examples | Isobutane conversion (%) | Isobutylene selectivity (%) | Isobutylene yield (%) |
|---|---|---|---|
| Comparative Example 1 | 34 | 90.8 | 30.9 |
| Comparative Example 2 | 33.5 | 94.6 | 31.7 |
| Example 1 | 40.7 | 95 | 38.6 |
| Example 2 | 41.1 | 94.5 | 38.8 |
| Example 3 | 39.5 | 96 | 37.9 |
| Example 4 | 44.6 | 93.3 | 41.6 |

The product stream of the Examples containing isobutylene and unconverted isobutane also included by-products such as methane, ethane, ethylene, propane, propylene, N-butane, 1-butene, cis-2-butene, and trans-2-butene. In Example 1, the selectivities of such by products were methane, 1.42%; ethane, 0.01%; ethylene, 0.03%; propane, 0.35%; propylene, 1.42%, N-butane, 0.34%; 1-butene, 0.57%; cis-2-butene, 0.7%; and trans-2-butene, 0.45.

This disclosure further encompasses the following aspects.

Aspect 1. An alkane dehydrogenation catalyst comprising: a support; and on the support, an active layer comprising gallium oxide, aluminum oxide, cerium oxide, a Group 1 metal oxide, and a Group 8-11 metal oxide.

Aspect 2. The alkane dehydrogenation catalyst of Aspect 1, wherein the support comprises alumina.

Aspect 3. The alkane dehydrogenation catalyst of Aspect 1, wherein the support comprises silica-modified alumina.

Aspect 4. The alkane dehydrogenation catalyst of any of the preceding aspects, wherein the active layer comprises, based on a total weight of the alkane dehydrogenation catalyst: 0.1 to 4.0 weight percent, or 0.2 to 3.5 weight percent, of the gallium oxide, 1 to 10 weight percent, or 2 to 8 weight percent, of the aluminum oxide, 0.1 to 3 weight percent, or 0.2 to 2.5 weight percent, of the cerium oxide, 0.1 to 2 weight percent, or 0.2 to 1.5 weight percent, of the Group 1 metal oxide, and 0.001 to 0.03 weight percent, or 0.002 to 0.02 weight percent, of the Group 8-11 metal oxide.

Aspect 5. The alkane dehydrogenation catalyst of any of the preceding aspects, wherein the Group 8-11 metal oxide comprises a Group 10 metal.

Aspect 6. The alkane dehydrogenation catalyst of any of the preceding aspects, wherein the Group 8-11 metal oxide comprises platinum.

Aspect 7. The alkane dehydrogenation catalyst of any of the preceding aspects, wherein the Group 1 metal oxide comprises potassium, sodium, cesium, or a combination thereof.

Aspect 8. The alkane dehydrogenation catalyst of any of the preceding aspects, wherein the Group 1 metal oxide comprises potassium.

Aspect 9. The alkane dehydrogenation catalyst of any of the preceding aspects, wherein the alkane dehydrogenation catalyst is in the form of an extrudate having a diameter of 1 to 4 millimeters, or 2 to 3.5 millimeters, and a length of 2 to 10 millimeters, or 3 to 9 millimeters.

Aspect 10. A method of forming an alkane dehydrogenation catalyst, the method comprising: forming an impregnation solution comprising a gallium precursor, an aluminum precursor, a cerium precursor, a Group 1 metal precursor, and a Group 8-11 metal precursor; contacting the impregnation solution with a catalyst support material to deposit gallium, aluminum, cerium, the Group 1 metal, and the Group 8-11 metal on the catalyst support material and form an impregnated support; drying the impregnated support to form a dried impregnated support; and calcining the dried impregnated support to form the alkane dehydrogenation catalyst.

Aspect 11. The method of Aspect 10, wherein the gallium precursor comprises a gallium nitrate, the aluminum precursor comprises an aluminum nitrate, the cerium precursor comprises a cerium nitrate, the Group 1 metal precursor comprises a Group 1 metal nitrate, and the Group 8-11 metal precursor comprises a Group 8-11 nitrate.

Aspect 12. The method of Aspect 10 or 11, wherein the support comprises alumina or silica-modified alumina, the Group 1 metal oxide comprises potassium, and the Group 8-11 metal oxide comprises platinum.

Aspect 13. An alkane dehydrogenation catalyst formed by the method of any of Aspects 10-12.

Aspect 14. A process of dehydrogenating an alkane, the process comprising: obtaining a catalyst comprising: a support, and on the support, an active layer comprising gallium oxide, aluminum oxide, cerium oxide, a Group 1 metal oxide, and a Group 8-11 metal oxide; and contacting the alkane dehydrogenation catalyst with a feed comprising the alkane at a temperature of 450 to 800° C., or 500 to 750° C., to produce a product stream comprising an alkene.

Aspect 15. The process of Aspect 14, wherein the active layer comprises, based on a total weight of the alkane dehydrogenation catalyst, 0.1 to 4.0 weight percent, or 0.2 to 3.5 weight percent, of the gallium oxide, 1 to 10 weight percent, or 2 to 8 weight percent, of the aluminum oxide, 0.1 to 3 weight percent, or 0.2 to 2.5 weight percent, of the cerium oxide, 0.1 to 2 weight percent, or 0.2 to 1.5 weight percent, of potassium metal oxide, and 0.001 to 0.03 weight percent, or 0.002 to 0.02 weight percent, of platinum oxide; and the support comprises alumina.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other (e.g., ranges of "up to 25 wt %, or, more specifically, 5 wt % to 20 wt %", are inclusive of the endpoints and all intermediate values of the ranges of "5 wt % to 25 wt %," etc.). "Combinations" is inclusive of blends, mixtures, alloys, reaction products, and the like. The terms "a" and "an" and "the" do not denote a limitation of quantity and are to be construed to cover both the singular and the plural, unless otherwise indicated herein or clearly contradicted by context. "Or" means "and/or" unless clearly stated otherwise. Reference throughout the specification to "some embodiments", "an embodiment", and so forth, means that a particular element described in connection with the embodiment is included in at least one embodiment described herein, and may or may not be present in other embodiments. In addition, it is to be understood that the described elements may be combined in any suitable manner in the various embodiments. A "combination thereof" is open and includes any combination comprising at least one of the listed components or properties optionally together with a like or equivalent component or property not listed.

Unless specified to the contrary herein, all test standards are the most recent standards in effect as of the filing date of this application, or, if priority is claimed, the filing date of the earliest priority application in which the test standard appears.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

Although the processes and methods of the present disclosure have been described with reference to exemplary embodiments thereof, the present disclosure is not limited to such exemplary embodiments and/or implementations. Rather, the processes and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

The invention claimed is:

1. An alkane dehydrogenation catalyst comprising:
a support; and
on the support, an active layer comprising
gallium oxide,
aluminum oxide,
cerium oxide,
a Group 1 metal oxide, and
a Group 8-11 metal oxide.

2. The alkane dehydrogenation catalyst of claim 1, wherein the support comprises alumina.

3. The alkane dehydrogenation catalyst of claim 1, wherein the support comprises silica-modified alumina.

4. The alkane dehydrogenation catalyst of claim 1, wherein the active layer comprises, based on a total weight of the alkane dehydrogenation catalyst:
0.1 to 4.0 weight percent of the gallium oxide,
1 to 10 weight percent of the aluminum oxide,
0.1 to 3 weight percent of the cerium oxide,
0.1 to 2 weight percent of the Group 1 metal oxide, and
0.001 to 0.03 weight percent of the Group 8-11 metal oxide.

5. The alkane dehydrogenation catalyst of claim 1, wherein the Group 8-11 metal oxide comprises a Group 10 metal.

6. The alkane dehydrogenation catalyst of claim 1, wherein the Group 8-11 metal oxide comprises platinum.

7. The alkane dehydrogenation catalyst of claim 1, wherein the Group 1 metal oxide comprises potassium, sodium, cesium, or a combination thereof.

8. The alkane dehydrogenation catalyst of claim 1, wherein the Group 1 metal oxide comprises potassium.

9. The alkane dehydrogenation catalyst of claim 1, wherein the alkane dehydrogenation catalyst is in the form of an extrudate having a diameter of 1 to 4 millimeters.

10. A method of forming an alkane dehydrogenation catalyst, the method comprising:
forming an impregnation solution comprising a gallium precursor, an aluminum precursor, a cerium precursor, a Group 1 metal precursor, and a Group 8-11 metal precursor;
contacting the impregnation solution with a catalyst support material to deposit gallium, aluminum, cerium, the Group 1 metal, and the Group 8-11 metal on the catalyst support material and form an impregnated support;
drying the impregnated support to form a dried impregnated support; and
calcining the dried impregnated support to form the alkane dehydrogenation catalyst.

11. The method of claim 10, wherein the gallium precursor comprises a gallium nitrate, the aluminum precursor comprises an aluminum nitrate, the cerium precursor comprises a cerium nitrate, the Group 1 metal precursor comprises a Group 1 metal nitrate, and the Group 8-11 metal precursor comprises a Group 8-11 nitrate.

12. The method of claim 10, wherein the support comprises alumina or silica-modified alumina, the Group 1 metal oxide comprises potassium, and the Group 8-11 metal oxide comprises platinum.

13. An alkane dehydrogenation catalyst formed by the method of claim 10.

14. A process of dehydrogenating an alkane, the process comprising:

obtaining a catalyst comprising:

a support, and on the support, an active layer comprising gallium oxide, aluminum oxide, cerium oxide, a Group 1 metal oxide, and a Group 8-11 metal oxide; and contacting the alkane dehydrogenation catalyst with a feed comprising the alkane at a temperature of 450 to 800° C. to produce a product stream comprising an alkene.

15. The process of claim 14, wherein the active layer comprises, based on a total weight of the alkane dehydrogenation catalyst, 0.1 to 4.0 weight percent of the gallium oxide, 1 to 10 weight percent of the aluminum oxide, 0.1 to 3 weight percent of the cerium oxide, 0.1 to 2 weight percent of potassium metal oxide, and 0.001 to 0.03 weight percent of platinum oxide; and the support comprises alumina.

\* \* \* \* \*